US011389447B2

(12) United States Patent
Baert et al.

(10) Patent No.: US 11,389,447 B2
(45) Date of Patent: *Jul. 19, 2022

(54) AQUEOUS SUSPENSIONS OF TMC278

(71) Applicant: Janssen Sciences Ireland Unlimited Company, County Cork (IE)

(72) Inventors: Lieven Elvire Colette Baert, Bruges (BE); Willy Albert Maria Carlo Dries, Merksplas (BE); Laurent Bruno Schueller, Antwerp (BE); Marc Karel Jozef Francois, Kapellen (BE); Peter Jozef Maria Van Remoortere, Kapellen (BE)

(73) Assignee: Janssen Sciences Ireland Unlimited Company, County Cork (IE)

( * ) Notice: Subject to any disclaimer, the term of this patent is extended or adjusted under 35 U.S.C. 154(b) by 8 days.

This patent is subject to a terminal disclaimer.

(21) Appl. No.: 14/964,297

(22) Filed: Dec. 9, 2015

(65) Prior Publication Data

US 2016/0089369 A1  Mar. 31, 2016

Related U.S. Application Data

(60) Continuation of application No. 14/493,525, filed on Sep. 23, 2014, now abandoned, which is a division of application No. 12/305,276, filed as application No. PCT/EP2007/056230 on Jun. 22, 2007, now abandoned.

(30) Foreign Application Priority Data

Jun. 23, 2006 (EP) .................... 06115398

(51) Int. Cl.
| | |
|---|---|
| A23K 50/10 | (2016.01) |
| A23K 20/158 | (2016.01) |
| A61K 31/505 | (2006.01) |
| A61K 9/00 | (2006.01) |
| A61K 9/14 | (2006.01) |
| A61K 31/00 | (2006.01) |
| A61K 47/10 | (2017.01) |
| A61K 47/34 | (2017.01) |

(52) U.S. Cl.
CPC .......... *A61K 31/505* (2013.01); *A61K 9/0019* (2013.01); *A61K 9/14* (2013.01); *A61K 9/145* (2013.01); *A61K 9/146* (2013.01); *A61K 31/00* (2013.01); *A61K 47/10* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 6,221,400 B1 | 4/2001 | Liversidge et al. | |
| 6,555,544 B2 * | 4/2003 | François | A61K 9/0019 |
| | | | 514/259.1 |
| 2004/0198739 A1 | 10/2004 | Guillemont et al. | |
| 2006/0111379 A1 | 5/2006 | Guillemont et al. | |

FOREIGN PATENT DOCUMENTS

| | | |
|---|---|---|
| EP | 0499299 | 8/1992 |
| EP | 0499299 | 8/2000 |
| EP | 1214059 | 6/2002 |
| WO | WO 2003/016306 A1 | 2/2003 |
| WO | WO 2003/043586 A | 5/2003 |
| WO | WO 2006/055603 A | 5/2006 |
| WO | WO 2006/106103 A2 | 10/2006 |
| WO | WO 2007/082922 A2 | 7/2007 |

OTHER PUBLICATIONS

Remington, *Farmacia*, 20th Edition, Chapter 22 (2003).
Tan et al., "Surface modification of nanoparticles by PEO/PPO block copolymers to minimize interactions with blood components and prolong blood circulation in rats", *Biomaterials* 1993, vol. 14, No. 11, pp. 823-833.
International search report dated Apr. 28, 2008, for corresponding international application PCT/EP2007/056230.
Van Eerdenbrugh et al., "Characterization of physic-chemical properties and pharmaceutical performance of sucrose co-freeze-dried solid nanparticulate powders of the anti-HIV agent loviride prepared by media milling", International Journal of Pharmaceutics, vol. 338, No. 1-2, pp. 198-206 (2007) (XP022093455).
Janssen et al., "In Search of a Novel Anti-HIV Drug: Multidisciplinary Coordination in the Discovery of 4-[[4-[[4-[(1E)-2-Cyanoethenyl]-2,6-dimethylphenyl]amino]-2-pyrimidinyl]amino]benzonitrile (R278474, Rillpivirine)", Journal of Medicinal Chemistry, vol. 48, No. 6, pp. 1901-1909 (2004) (XP008050052).
Merisko-Liversidge et al., "Nanosizing: a formulation approach for poorly-water-soluble compounds", European Journal of Pharmaceutical Sciences, vol. 18, pp. 113-120 (2003) (XP002399359).
Müller et al., "Nanosuspensions as particulate drug formulations in therapy Rationale for development and what we can expect for the future", Advanced Drug Delivery Reviews, vol. 47, No. 1, pp. 3-19 (2001) (XP002232883).
Gregoriadis, et al., "Targeting of Drugs 6 Strategies for Stealth Therapeutic Systems," Life Science, 300: 4-5 (1998).
Silvestri, et al., "Current state-of-the-art in preclinical and clinical development of novel nonnucleotide HIV-1 reverse transcriptase inhibitors," Expert Opinion on Therapeutic Patents, 16(7): 939-962 (2006).
Janssen et al., "In Search of a Novel Anti-HIV Drug: Multidisciplinary Coordination in the Discovery of 4-[[4-[[4-[(1 E)-2-Cyanoethenyl]-2,6- dimethylphenyl]amino]-2-pyrimidinyl]amino]benzonitrile (R278474, Rilpivirine)", J. Med. Chem., (2005), vol. 48, No. 6, pp. 1901-1909.

(Continued)

*Primary Examiner* — Layla Soroush
(74) *Attorney, Agent, or Firm* — Sofia Kopelevich

(57) ABSTRACT

This invention concerns pharmaceutical compositions for administration via intramuscular or subcutaneous injection, comprising micro- or nanoparticles of the NNRTI compound TMC278, suspended in an aqueous pharmaceutically acceptable carrier, and the use of such pharmaceutical compositions in the treatment and prophylaxis of HIV infection.

23 Claims, No Drawings

(56) References Cited

OTHER PUBLICATIONS

Declaration: Entitlement to apply for and be granted a patent in relation to International Application No. PCT/EP2007/056230.
Patent Assignment from Tibotec BVBA to Tibotec Pharmaceuticals Limited executed Jul. 23, 2007 for Application No. 12305276.
Patent Assignment from Janssen Pharmaceutica NV to Tibotec Pharmaceuticals Limited executed Jul. 23, 2007 for Application No. 12305276.
NIH Guidelines for the Use of Antiretroviral Agents in H IV-1-Infected Adults and Adolescent dated May 4, 2006.
Janssen Press Release dated Aug. 15, 2018, Janssen Reports Positive Topline Results for ATLAS Phase III Study of a Novel, Long Acting injectable Two-Drug Regimen for the Treatment of HIV-1.
Janssen Press Release dated Apr. 29, 2019, Janssen Announces Submission of New Drug Application to U.S. FDA for the First Monthly, Injectable, Two-Drug Regimen of Rilpivirine and Cabotegravir for Treatment of HIV.
Priority document downloaded from EPO Register in Patent Application No. 06115938.0/EP06115938.
Request for grant of a European patent for EP06115938 printed on Jun. 23, 2006.
Acknowledgement of Receipt issued by the EPO for EP06115938, date of receipt Jun. 23, 2006.
PCT Request Form for International Application No. PCT/EP2007/056230, International Filing Date Jun. 22, 2007.
Remington, The Science and Practice of Pharmacy, 21$^{st}$ Edition, pp. 314, 320, 749, 766, 955,1072 (2005).
Uranyl Acetate MSDS (2006), EMS Catalog No. 22400, Dated May 15, 2006.
Frampton & Croom, "Efavirenz/Emtricitabine/Tenofovir Disoproxil Fumarate" Drugs 66, 1501-1512 (2006).
Extract from Organic Chemistry by Clayden, Greeves, Warren and Wothers, pp. 583-585; 748-749; 758-759 (2004).
Aulton, Michael E., Pharmaceutics, The Science of Dosage Form Design, 2nd Edition, Table of Contents (2002).
Baert, Lieven et al., Development of a long-acting injectable formulation with nanoparticles of rilpivirine (TMC278) for HIV treatment, European Journal of Pharmaceutics and Biopharmaceutics 72 (2009) pp. 502-508.
Gregoriadis, G. et al. (eds.), "Coating of Nanoparticles With Surfactants: Targeting Versus Prolonged Circulation", *Targeting of Drugs 6*, (1998), pp. 253-261.
Verloes, R. et al., "Safety, Tolerability and Pharmacokinetics of Rilpivirine Following Administration of a Long-Acting Formulation in Healthy Volunteers", *HIV Medicine* (2015), 16, pp. 477-484.
Notice of Opposition in European Patent No. EP2040671 dated Oct. 30, 2018 (16 pages).
Rabinow, Barrett E., "Nanosuspensions in Drug Delivery", Nature Reviews, Sep. 2004, vol. 3, pp. 785-796.
Caelyx package leaflet, May 23, 2006.
Edurant package leaflet, Nov. 30, 2011.
Eldred et al., Journal of Acquired Immune Deficiency Syndromes and Human Retrovirology, vol. 18, No. 2, Jun. 1, 1998, pp. 117-125.
Gallant et al., J. Int. Assoc. Physicians AIDS Care, May 1998, 4(5): 32-5 (abstract only).
Golin et al., J. Gen. Intern. Med., Oct. 2002, vol. 17, pp. 756-765.
Haldol® decanoate FDA approval material, Center for Drug Evaluation and Research, Approval Package, Jan. 30, 1998.
Merisko-Liversidge et al., European Journal of Pharmaceutical Sciences, 18 (2003) pp. 113-120.
Opposition Decision, EP1827500, T 2506/12; Oct. 4, 2016, one page document.
Risperdal Consta® product information, Janssen, L.P., Mar. 2006.
The PRN Notebook®; vol. 11, No. 2; Oct. 2006, pp. 2-7.
Torchilin, V., Nature Reviews, "Recent Advances with Liposomes as Pharmaceutical Carriers", vol. 4, pp. 145-160, Feb. 2005.

\* cited by examiner

AQUEOUS SUSPENSIONS OF TMC278

CROSS-REFERENCE TO RELATED APPLICATIONS

This application is continuation of U.S. application Ser. No. 14/493,525, filed Sep. 23, 2014, which is a divisional of U.S. application Ser. No. 12/305,276, filed 17 Dec. 2008, which is a national stage application of International Patent Application Number PCT/EP2007/056230, filed 22 Jun. 2007, which claims priority to European Patent Application Number 06115398.0, filed 23 Jun. 2006. The entire contents of each of the aforementioned applications are incorporated herein by reference in their entireties.

FIELD OF THE INVENTION

This invention concerns pharmaceutical compositions for administration via intramuscular or subcutaneous injection, comprising micro- or nanoparticles of the NNRTI compound TMC278, suspended in an aqueous pharmaceutically acceptable carrier, and the use of such pharmaceutical compositions in the treatment and prophylaxis of HIV infection.

BACKGROUND OF THE INVENTION

The treatment of Human Immunodeficiency Virus (HIV) infection, known as cause of the acquired immunodeficiency syndrome (AIDS), remains a major medical challenge. HIV is able to evade immunological pressure, to adapt to a variety of cell types and growth conditions and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtR-TIs), HIV-protease inhibitors (PIs) and the more recent fusion inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retroviral Therapy) resulted in a remarkable improvement in anti-HIV therapy, leading to a dramatic reduction in HIV-associated morbity and mortality. Current guidelines for antiretroviral therapy recommend such triple combination therapy regimen even for initial treatment. However, none of the currently available drug therapies is capable of completely eradicating HIV. Even HAART can face the emergence of resistance, often due to non-adherence and non-persistence with antiretroviral therapy. In these cases HAART can be made effective again by replacing one of its components by one of another class. If applied correctly, treatment with HAART combinations can suppress the virus for many years, up to decades, to a level where it no longer can cause the outbreak of AIDS.

One class of HIV drugs often used in HAART is that of the NNRTIs, a number of which are currently on the market and several others are in various stages of development. An NNRTI currently in development is the compound 4-[[4-[[4-(2-cyanoethenyl)-2,6-dimethylphenyl]-amino]-2-pyrimidinyl]-amino]-benzonitrile, also referred to as TMC278. This compound not only shows pronounced activity against wild type HIV, but also against many of its mutated variants. The compound TMC278, its pharmacological activity as well as a number of procedures for its preparation have been described in WO 03/16306. Various conventional pharmaceutical dosage forms, including tablets, capsules, drops, suppositories, oral solutions and injectable solutions are exemplified therein.

Because of their pharmacokinetic properties and the need to keep plasma levels above a minimum level, currently used anti-HIV drugs require frequent administration of relatively high doses. The number and/or volume of dosage forms that need to be administered are commonly referred to as "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this also leads to the emergence of viral resistance. The problems associated with a high pill burden are prominent in anti-HIV therapy where a patient must take a large number of different anti-HIV agents.

Therefore, it would be desirable to provide HIV inhibitory therapy that reduces pill burden in that it involves the administration of dosage forms of relatively small size and additionally does not require frequent dosing. It would be attractive to provide anti-HIV therapy involving the administration of dosage forms at long time intervals such as one week or longer, or even one month or longer.

HIV can never completely be eradicated so that persons infected with HIV pose a continuous risk of infecting others. After initial infection it takes a long time before the outbreak of the first symptoms of AIDS. People may live for years with the infection without experiencing any effects of it thereby being unaware of the risk of further transferring the virus to others. Prevention of HIV transmission therefore is crucial.

Prevention currently focuses on avoiding transmission by sexual contacts, in particular by the use of condoms in populations at risk of being infected, on careful monitoring of blood samples for the presence of HIV and on avoiding of contact with blood of potentially infected subjects.

Despite these measures there is always an imminent risk of individuals being in contact with HIV infected persons of becoming infected. This in particular is the case for those providing medical care to infected patients or patients at risk of being infected such as physicians, nurses or dentists. Another group of individuals at risk are breast-fed infants whose mother is infected or at risk of becoming infected, especially in developing countries where alternatives for breast-feeding are less obvious.

Hence there is a need for further means that provide prevention against transmission of HIV. There is a particular need for effective prevention means that are easy to apply. Providing such prevention means is another object of the present invention.

It now has been found that the compound TMC278 can be formulated into micro- or nanoparticles and that such formulations can be used as depot formulations, which may find use in the treatment of HIV infection as well as in the prevention against transmission of HIV. Nanoparticles are known in the prior art, having been described, for example, in EP-A-0 499 299. Such particles have an average particle size in the submicron range and consist of particles of a crystalline drug substance having a surface modifier adsorbed on their surface. Nanoparticles have been used to formulate poorly water-soluble active ingredients.

The invention furthermore relates to the intermittent administration of these micro- or nanoparticle formulations at time intervals of one week or longer that result in plasma levels that may be sufficient to suppress the growth of HIV. This allows for a reduced number of administrations thereby being beneficial in terms of pill burden and drug compliance of the patient. The micro- or nanoparticle formulations of TMC278 of the invention therefore may be useful in the long-term treatment of HIV infection.

The intermittent administration of micro- or nanoparticle formulations of TMC278 at time intervals of one week or longer furthermore results in plasma levels that may be sufficient to provide prevention against transmission of HIV. Also in this instance, a reduced number of administrations are required, which again is advantageous in terms of pill burden and drug compliance of the individual at risk of being infected.

SUMMARY OF THE INVENTION

The present invention is concerned with a pharmaceutical composition for administration by intramuscular or subcutaneous injection, comprising a therapeutically effective amount of TMC278, a salt, a stereoisomer or a stereoisomeric mixture thereof, in the form of a suspension of micro- or nanoparticles comprising:

(a) TMC278, a salt, a stereoisomer or a stereoisomeric mixture thereof, in micro- or nanoparticle form, having a surface modifier adsorbed to the surface thereof; and
(b) a pharmaceutically acceptable aqueous carrier; wherein the TMC278 active ingredient is suspended.

The invention further concerns a method of treating a subject infected with HIV, said method comprising the administration, by intramuscular or subcutaneous injection, of an anti-HIV effective amount pharmaceutical composition as specified above or hereinafter. Or, alternatively, the invention concerns the use of a pharmaceutical composition as specified above or hereinafter, for the manufacture of a medicament for treating HIV infection. In one embodiment, the composition is for the long-term treatment of HIV infection.

In another aspect, there is provided a method for the long term treatment of a subject infected with HIV, said method comprising the administration of an effective amount of a pharmaceutical composition as specified above or hereinafter, for administration by intramuscular or subcutaneous injection; wherein the composition is administered or is to be administered intermittently at a time interval that is in the range of one week to one year, or one week to two years. Or, alternatively, the invention concerns the use of a pharmaceutical composition as specified above or hereinafter, for the manufacture of a medicament for the long term treatment of a subject infected with HIV, for administration by intramuscular or subcutaneous injection, wherein the composition is administered or is to be administered intermittently at a time interval that is in the range of one week to one year, or one week to two years.

The invention further concerns a method for the prevention of HIV infection in a subject at risk of being infected by HIV, said method comprising administering an amount, effective in preventing HIV infection, of a pharmaceutical composition as specified above or as further specified hereinafter, to said subject. Or alternatively, the invention concerns the use of a pharmaceutical composition as specified above or as further specified hereinafter for the manufacture of a medicament for the prevention of HIV infection in a subject at risk of being infected by HIV.

In another aspect the invention relates to a method for the long term prevention of HIV infection in a subject at risk of being infected by HIV, said method comprising administering to said subject an effective amount of a pharmaceutical composition as specified above or as further specified hereinafter, wherein the composition is administered or is to be administered intermittently at a time interval that is in the range of one week to one year, or one week to two years.

The present invention furthermore relates to the use of a pharmaceutical composition as specified above or as further specified hereinafter, for the manufacture of a medicament for the long term prevention for the long term prevention of HIV infection in a subject at risk of being infected by HIV, wherein the composition is administered or is to be administered intermittently at a time interval that is in the range of one week to one year or one week to two years.

In one embodiment the invention concerns a use or a method as specified herein, wherein the pharmaceutical composition is administered or is to be administered at a time interval that is in the range of one week to one month, or in the range of one month to three months, or in the range of three months to six months, or in the range of six months to twelve months, or in the range of 12 months to 24 months.

In another embodiment the invention concerns a use or a method as specified herein, wherein the pharmaceutical composition is administered or is to be administered once every two weeks, or once every month, or once every three months.

Further pharmaceutical compositions, methods of treatment or prevention, as well as uses for the manufacture of medicaments based on these compositions will be described hereinafter and are meant to be part of the present invention.

DETAILED DESCRIPTION OF THE INVENTION

The compound used in the invention is the compound TMC278 (also referred to as 8278474 or rilpivirine) or 4-[[4-[[4-(2-cyanoethenyl)-2,6-dimethylphenyl]amino]-2-pyrimidinyl]amino]benzonitrile.

TMC278 can be used in base form or as a suitable pharmaceutically acceptable addition salt form, such as an acid addition salt form. The pharmaceutically acceptable addition salts are meant to comprise the therapeutically active non-toxic salt forms. The acid addition salt forms can be obtained by treating the base form with appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and the like acids. In one embodiment, the TMC278 active ingredient used is the base form of TMC278.

The term "addition salt" also comprises pharmaceutically acceptable hydrates and solvent addition forms that the compound TMC278 is able to form. Examples of such forms are e.g. hydrates, alcoholates and the like.

TMC278 occurs in stereoisomeric forms, more in particular as E- and Z-isomeric forms. Both isomers may be used in the present invention. Whenever reference is made herein to TMC278, the E- or the Z-form as well as any mixture of both forms are meant to be included. A preferred form of TMC278 for use in the invention is the E-isomer, i.e. (E)-4-[[4-[[4-(2-cyanoethenyl)-2,6-dimethylphenyl]-amino]-2-pyrimidinyl]-amino]-benzonitrile, which may be referred to as E-TMC278. The Z-isomer of TMC278, i.e. (Z)-4-[[4-[[4-(2-cyanoethenyl)-2,6-dimethylphenyl]-amino]-2-pyrimidinyl]-amino]-benzonitrile, which may be referred to as Z-TMC278), can also be used.

Whenever reference is made herein to the E-form of TMC278 (i.e. E-TMC278), the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of TMC278 (i.e. Z-TMC278), the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. The Z-form substantially free of the E-form can also be used. Substantially free in this context refers to E-Z-mixtures with no or almost no E-form, e.g. isomeric mixtures containing as much as 90%, in particular 95% or even 98% or 99% of the Z-form. In one embodiment, the TMC278 active ingredient used is the E-form of TMC278, in particular the E-form of TMC278 base.

Also meant to be included for use in this invention are salts of the stereoisomeric forms of TMC278, in particular the salts mentioned above of Z-TMC278 or of E-TMC278.

Whenever used herein, the term "TMC278" refers to as well the base form as any pharmaceutically acceptable acid-addition salt thereof, and also to the stereoisomeric forms of TMC278 as well as any pharmaceutically acceptable acid-addition salt of said stereoisomeric forms. In particular, the term "TMC278" refers to the E-isomer of TMC278 as well as its pharmaceutically acceptable acid-addition salts. The term "TMC278" may also refer to the base form of the E-isomer of TMC278.

It has been found that the physico-chemical properties of TMC278 allow for the manufacture of micro- or nanoparticle suspensions that have unique pharmacokinetic properties in that they can be used for the long-term treatment of HIV infection as well as in the long-term prevention of HIV infection and to this purpose only a limited number of drug administrations is required. This is beneficial in terms of pill-burden as well as patient compliance with the prescribed dose regimen.

As used herein the term "treatment of HIV infection" relates to the treatment of a subject being infected with HIV. The term "treatment of HIV infection" also relates to the treatment of diseases associated with HIV infection, for example AIDS, or other conditions associated with HIV infection including thrombocytopaenia, Kaposi's sarcoma and infection of the central nervous system characterized by progressive demyelination, resulting in dementia and symptoms such as, progressive dysarthria, ataxia and disorientation, and further conditions where HIV infection has also been associated with, such as peripheral neuropathy, progressive generalized lymphadenopathy (PGL), and AIDS-related complex (ARC).

The term "prevention of HIV infection" relates to the prevention or avoidance of a subject becoming infected with HIV. The source of infection can be various, a material containing HIV, in particular a body fluid that contains HIV such as blood or sperm, or another subject who is infected with HIV. Prevention of HIV infection relates to the prevention of the transmission of the virus from the material containing HIV or from the HIV infected individual to an uninfected person, or relates to the prevention of the virus from entering the body from an uninfected person. Transmission of the HIV virus can be by any known cause of HIV transfer such as by sexual transmission or by contact with blood of an infected subject, e.g. medical staff providing care to infected subjects. Transfer of HIV can also occur by contact with HIV infected blood, e.g. when handling blood samples or with blood transfusion. It can also be by contact with infected cells, e.g. when carrying out laboratory experiments with HIV infected cells.

The terms "treatment of HIV infection", "anti-HIV therapy", as well as similar terms, refer to a treatment by which the viral load of HIV (represented as the number of copies of viral RNA in a specified volume of serum) is reduced. The more effective the treatment, the lower the viral load. Preferably the viral load should be reduced to as low levels as possible, e.g. below about 200 copies/ml, in particular below about 100 copies/ml, more in particular below 50 copies/ml, if possible below the detection limit of the virus. Reductions of viral load of one, two or even three orders of magnitude (e.g. a reduction in the order of about 10 to about $10^2$, or more, such as about $10^3$) are an indication of the effectiveness of the treatment. Another parameter to measure effectiveness of anti-HIV treatment is the CD4 count, which in normal adults ranges from 500 to 1500 cells per µl. Lowered CD4 counts are an indication of HIV infection and once below about 200 cells per µl, AIDS may develop. An increase of CD4 count, e.g. with about 50, 100, 200 or more cells per µl, is also an indication of the effectiveness of anti-HIV treatment. The CD4 count in particular should be increased to a level above about 200 cells per µl, or above about 350 cells per µl. Viral load or CD4 count, or both, can be used to diagnose the degree of HIV infection.

The terms "effective treatment of HIV" and similar terms refer to that treatment that lowers the viral load, or increases CD4 count, or both, as described above. The terms "effective prevention of HIV" and similar terms refer to that situation where there is a decrease in the relative number of newly infected subjects in a population in contact with a source of HIV infection such as a material containing HIV, or a HIV infected subject. Effective prevention can be measured, for example, by measuring in a mixed population of HIV infected and non-infected individuals, if there is a decrease of the relative number of newly infected individuals, when comparing non-infected individuals treated with a pharmaceutical composition of the invention, and non-treated non-infected individuals. This decrease can be measured by statistical analysis of the numbers of infected and non-infected individuals in a given population over time.

The terms "therapeutically effective amount", "an amount, effective in preventing HIV infection", and similar terms, refer to amounts of the active ingredient TMC278 that result in efficacious blood plasma levels. With "efficacious blood plasma levels" is meant those blood plasma levels of the HIV inhibitor TMC278 that provide effective treatment or effective prevention of HIV infection.

The term "subject" in particular relates to a human being.

The term "micro- or nanoparticles" refers to particles in the micrometer or nanometer range. The size of the particles should be below a maximum size above which administration by subcutaneous or intramuscular injection becomes impaired or even no longer is possible. Said maximum size depends for example on the limitations imposed by the needle diameter or by adverse reactions of the body to large particles, or both. In one embodiment, the pharmaceutical compositions of the invention comprise TMC278 in nanoparticle form.

The average effective particle size of the micro- or nanoparticles of the present invention may be below about 50 µm, or below about 20 µm, or below about 10 µm, or below about 1000 nm, or below about 500 nm, or below about 400 nm, or below about 300 nm, or below about 200 nm. The lower limit of the average effective particle size may be low, e.g. as low as about 100 nm or as low as about 50 nm. In one embodiment, the average effective particle size is in the range of about 50 nm to about 50 µm, or about 50 nm to about 20 µm, or about 50 nm to about 10 µm, or about 50 nm to about 1000 nm, about 50 nm to about 500 nm, or about 50 nm to about 400 nm, or about 50 nm to about 300 nm, or about 50 nm to about 250 nm, or about 100 nm to about 250 nm, or about 150 nm to about 220 nm, or 100 to 200 nm, or about 150 nm to about 200 nm, e.g. about 130 nm, or about 150 nm.

As used herein, the term average effective particle size has its conventional meaning as known to the person skilled in the art and can be measured by art-known particle size measuring techniques such as, for example, sedimentation field flow fractionation, photon correlation spectroscopy, laser diffraction or disk centrifugation. The average effective particle sizes mentioned herein may be related to volume distributions of the particles. In that instance, by "an effective average particle size of less than about 50 µm" it is meant that at least 50% of the volume of the particles has a particle size of less than the effective average of 50 µm, and the same applies to the other effective particle sizes mentioned. In a similar manner, the average effective particle sizes may be related to weight distributions of the particles but usually this will result in the same or about the same value for the average effective particle size.

The pharmaceutical compositions of the present invention provide release of the active ingredient TMC278 over a prolonged period of time and therefore they can also be referred to as sustained or delayed release compositions. After administration, the compositions of the invention stay in the body and steadily release TMC278, keeping such levels of this active ingredient in the patient's system for a prolonged period of time, thereby providing, during said period, anti-HIV therapy or prevention of HIV infection. Because of the fact that the pharmaceutical compositions of the invention stay in the body and steadily release TMC278, they can be referred to as pharmaceutical compositions suitable as depot formulations.

As used herein with the term "prolonged period of time", there is meant a term (or time period) that may be in the range of one week up to one year or up to two years, or a term in the range of one to two weeks, or two to three weeks, or three to four weeks, or a term in the range of one to two months, or two to three months, or three to four months, or three to six months, or six months to 12 months, or 12 months to 24 months, or a term that is in the range of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months.

The pharmaceutical compositions of this invention may be applied in the long-term treatment or the long-term prevention of HIV infection, or with other words they may be used in the treatment of HIV infection, or in the prevention of HIV infection, during a prolonged period of time. The compositions of the invention are effective in anti-HIV therapy or in the prevention of HIV infection for a prolonged period of time, for example for at least about one week or longer, or for about 1 month or longer. By the expression "effective for at least about one week or longer", one means that the plasma level of the active ingredient, TMC278, should be above a threshold value. In case of therapeutic application said threshold value is the lowest plasma level at which TMC278 provides effective treatment of HIV infection. In case of application in the prevention of HIV infection said threshold value is the lowest plasma level at which TMC278 is effective in preventing transmission of HIV infection.

With "long term" for example as used in relation to "long term prevention of HIV infection" or "long term treatment of HIV infection", or similar terminology, there are meant terms that may be in the range of one week up to one year or up to two years, or longer, such as five or 10 years. In particular in the case of treatment of HIV infection, such terms will be long, in the order of one to several years. Such terms may also be relatively short, in particular in the case of prevention. Shorter terms are those of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months. In one embodiment the methods and uses in accordance with the present invention are for the prevention of HIV infection during one month, or several months, e.g. 2, 3, 4, 5 or six months or even longer, e.g. 7, 8, 9 or 12 months.

The pharmaceutical compositions of the present invention can be administered at various time intervals. When used in the prevention of HIV infection, the pharmaceutical compositions of this invention can be administered only once or a limited number of times such as twice, three, four, five or six times, or more. This may be recommendable where prevention is required during a limited period of time, such as the period during which there is a risk of infection.

The pharmaceutical compositions of the present invention can be administered at the time intervals mentioned above, such as at a time interval that is in the range of one week to one month, or in the range of one month to three months, or in the range of three months to six months, or in the range of six months to twelve months. In one embodiment, the pharmaceutical composition can be administered once every two weeks, or once every month, or once every three months. In another embodiment the time interval is in the range of one to two weeks, or two to three weeks, or three to four weeks, or the time interval is in the range of one to two months, or two to three months, or three to four months, or three to six months, or six months to 12 months, or 12 months to 24 months. The time interval may be at least one week, but may also be several weeks, e.g. 2, 3, 4, 5 or 6 weeks, or at time intervals of one month, or of several months, e.g. 2, 3, 4, 5 or 6 months or even longer, e.g. 7, 8, 9 or 12 months. In one embodiment, the pharmaceutical compositions of the present invention are administered at a time interval of one, two or three months. These longer periods between each administration of the pharmaceutical compositions of the invention provide further improvements in terms of pill burden and compliance. To further improve compliance, patients can be instructed to take their medication at a certain day of the week, where the composition is administered on a weekly schedule, or at a certain day of the month in case of a monthly schedule.

The length of the time intervals between each administration of a composition of the present invention may vary. For example said time intervals may be selected in function of the blood plasma levels. The intervals may be shorter where the blood plasma levels of TMC278 are deemed too low, e.g. when these approach the minimum blood plasma level specified hereinafter. The intervals may be longer where the blood plasma levels of TMC278 are deemed too high. In one embodiment, the compositions of the invention are administered at equal time intervals. The compositions may be administered without any interjacent additional administrations, or with other words, the compositions may be administered at particular points in time separated from one another by a time period of varying or equal length, e.g. a time period of at least one week, or any other time period specified herein, during which no further TMC278 is administered. Having time intervals of the same length has the advantage that the administration schedule is simple, e.g. administration takes place at the same day in the week, or the same day in the month. Such administration schedule therefore involves limited "pill burden" thereby contributing beneficially to the patient's compliance to the prescribed dosing regimen.

The concentration (or "C") of TMC278 in the blood plasma of a subject treated therewith is generally expressed as mass per unit volume, typically nanograms per milliliter (ng/ml). For convenience, this concentration may be referred to herein as "blood plasma drug concentration" or "blood plasma concentration".

The dose (or amount) of TMC278 administered, depends on the amount of TMC278 in the pharmaceutical compositions of the invention, or on the amount of a given composition that is administered. Where higher blood plasma levels are desired, either or both of a composition of higher TMC278 concentration, or more of a given composition, may be administered. This applies vice versa if lower plasma levels are desired. Also a combination of varying time intervals and varying dosing may be selected to attain certain desired blood plasma levels.

The dose (or amount) of TMC278 administered also depends on the frequency of the administrations (i.e. the time interval between each administration). Usually, the dose will be higher where administrations are less frequent. All these parameters can be used to direct the blood plasma levels to desired values The dosing regimen also depends on whether prevention or treatment of HIV infection is envisaged. In case of therapy, the dose of TMC278 administered or the frequency of dosing, or both, are selected so that the blood plasma concentration of TMC278 is kept above a minimum blood plasma level. The term "minimum blood plasma level" (or $C_{min}$) in this context refers to the blood plasma level of TMC278 that provides effective treatment of HIV. In particular, the blood plasma level of TMC278 is kept at a level above a minimum blood plasma level of about 10 ng/ml, or above about 15 ng/ml, or above about 20 ng/ml, or above about 40 ng/ml. The blood plasma level of TMC278 may be kept above a minimum blood plasma level that is higher, for example above about 50 ng/ml, or above about 90 ng/ml, or above about 270 ng/ml, or above about 540 ng/ml In one embodiment, the blood plasma level of TMC278 is kept above a level of about 13.5 ng/ml, or is kept above a level of about 20 ng/ml. Or the blood plasma level of TMC278 may be kept within certain ranges, in particular ranges starting from a minimum blood plasma level selected from those mentioned above and ending at a higher blood plasma levels selected from those mentioned above and selected from 500 ng/ml and 1000 ng/ml (e.g. from 10 to 15, 10 to 20, 10 to 40, etc., or from 15 to 20, or 15 to 40, or 15 to 90, etc., or 20 to 40, 20 to 90, or 20 to 270, etc., or 40 to 90, 40 to 270, or 40-540, etc., each time from about the indicated value in ng/ml to about the indicated value in ng/ml). In one embodiment said range is from about 10 to about 20, from about 20 to about 90, from 90 to 270, from 270 to 540, from 540 to 1000, each time from about the indicated value in ng/ml to about the indicated value in ng/ml.

The plasma levels of TMC278 should be kept above the above-mentioned minimum blood plasma levels because at lower levels the virus may no longer be sufficiently suppressed so that it can multiply with the additional risk of the emergence of mutations.

In the instance of HIV prevention, the term "minimum blood plasma level" (or $C_{min}$) refers to the lowest blood plasma level of TMC278 that provides effective prevention of HIV infection. In the case of transmission of HIV from a material containing HIV or from a subject infected by HIV to a subject not infected by HIV, this is the lowest blood plasma level that is effective in inhibiting said transmission.

In particular, in the instance of HIV prevention, the blood plasma level of TMC278 can be kept at a level above a minimum blood plasma level mentioned above in relation to therapy. However in prevention the blood plasma level of TMC278 can be kept at a lower level, for example at a level above about 4 ng/ml, or about 5 ng/ml, or about 8 ng/ml. The blood plasma levels of TMC278 should preferably be kept above these minimum blood plasma levels because at lower levels the drug may no longer be effective thereby increasing the risk of transmission of HIV infection. Plasma levels of TMC278 may be kept at somewhat higher levels to have a safety margin. Such higher levels start from about 50 ng/ml or more. The blood plasma level of TMC278 can be kept at a level that is in the ranges mentioned above in relation to therapy, but where the lower limits include the blood plasma levels of about 4 ng/ml, or about 5 ng/ml, or about 8 ng/ml.

An advantage of TMC278 is that it can be used up to relatively high blood plasma levels without any significant side effects. The plasma concentrations of TMC278 may reach be relatively high levels, but as with any drug should not exceed a maximum plasma level (or $C_{max}$), which is the blood plasma level where TMC278 causes significant side effects. As used herein, the term "significant side effects" means that the side effects are present in a relevant patient population to an extent that the side effects affect the patients' normal functioning. The $C_{max}$ for TMC278 can be determined from the extrapolation of test data in cellular assays or from the evaluation of clinical testing and preferably should not exceed a value of about 500 ng/ml or 1000 ng/ml. In an embodiment, the amount and the frequency of administrations of TMC278 to be administered are selected such that the blood plasma concentrations are kept during a long term at a level comprised between a maximum plasma level (or $C_{max}$ as specified above) and a minimum blood plasma level (or $C_{min}$ as specified above).

In certain instances it may be desirable to keep the plasma levels of TMC278 at relatively low levels, e.g. as close as possible to the minimum blood plasma levels specified herein. This will allow reducing the frequency of the administrations and/or the quantity of TMC278 administered with each administration. It will also allow avoiding undesirable side effects, which will contribute to the acceptance of the dosage forms in most of the targeted population groups who are healthy people at risk of being infected and therefore are less inclined to tolerate side effects. The plasma levels of TMC278 may be kept at relatively low levels in the instance of prevention. One embodiment concerns uses or methods for prevention of HIV infection, as specified above or hereinafter, wherein the minimum blood plasma level of TMC278 is as specified herein and the maximum blood plasma level is about equal to the lowest blood plasma level that causes the RT inhibitor to act therapeutically, also as specified herein.

In other embodiments, the blood plasma level of TMC278 is kept at a level below a lower maximum blood plasma level of about 10 ng/ml, more in particular about 15 ng/ml, further in particular about 20 ng/ml, still more in particular about 40 ng/ml. In a particular embodiment, the blood plasma level of TMC278 is kept below a level of about 13.5 ng/ml. In one embodiment, the plasma level of TMC 278 is kept in an interval of the lower maximum blood level specified above, and the minimum blood plasma levels mentioned in relation to prevention. For example the blood plasma levels of TMC278 are kept below about 10 ng/ml and above a minimum level of about 4 ng/ml.

In other instances it may be desirable to keep the plasma levels of TMC278 at relatively higher levels, for example where there is a high risk of infection and more frequent and/or higher doses are not an issue. In these instances the minimum blood plasma level may be equal to the lowest blood plasma level of TMC278 that provides effective treatment of HIV, such as the specific levels mentioned herein.

In the instance of prevention, the dose to be administered should be calculated on a basis of about 0.2 mg/day to about 50 mg/day, or 0.5 mg/day to about 50 mg/day, or of about 1 mg/day to about 10 mg/day, or about 2 mg/day to about 5 mg/day, e.g. about 3 mg/day. This corresponds to a weekly dose of about 1.5 mg to about 350 mg, in particular of about 3.5 mg to about 350 mg, in particular of about 7 mg to about 70 mg, or about 14 mg to about 35 mg, e.g. about 35 mg, or to a monthly dose of from 6 mg to about 3000 mg, in particular about 15 mg to about 1,500 mg, more in particular of about 30 mg to about 300 mg, or about 60 mg to about 150 mg, e.g. about 150 mg. Doses for other dosing regimens can be readily calculated by multiplying the daily dose with the number of days between each administration.

In the instance of therapy, the dose to be administered should be somewhat higher and should be calculated on a basis of about 1 mg/day to about 150 mg/day, or of about 2 mg/day to about 100 mg/day, or of about 5 mg/day to about 50 mg/day, or about 10 mg/day to about 25 mg/day, e.g. about 15 mg/day. The corresponding weekly or monthly doses can be calculated as set forth above. For applications in prevention, the doses may be lower although the same dosing as for therapeutic applications may be used.

It has been found that, once administered, the blood plasma levels of TMC278 are more or less stable, i.e. they fluctuate within limited margins. The blood plasma levels have been found to approach more or less a steady state mode or to approximate more or less a zero order release rate during a prolonged period of time. By "steady state" is meant the condition in which the amount of drug present in the blood plasma of a subject stays at more or less the same level over a prolonged period of time. The plasma levels of TMC278 generally do not show any drops below the minimum plasma level at which the drug is effective. The term "stays at more or less the same level" does not exclude that there can be small fluctuations of the plasma concentrations within an acceptable range, e.g. fluctuations within a range of about +/−30%, or about +/−20%, or about +/−10%, or about +/−10%.

In some instances there may be an initial plasma concentration peak after administration, after which the plasma levels achieve a "steady-state", as mentioned hereinafter.

The compositions of the invention show good local tolerance and ease of administration. Good local tolerance relates to minimal irritation and inflammation at the site of injection; ease of administration refers to the size of needle and length of time required to administer a dose of a particular drug formulation. In addition, the compositions of the invention show good stability and have an acceptable shelf life.

The micro- or nanoparticles of the present invention have a surface modifier adsorbed on the surface thereof. The function of the surface modifier is to act as a wetting agent as well as a stabilizer of the colloidal suspension.

In one embodiment, the micro- or nanoparticles in the compositions of the invention mainly comprise crystalline TMC278 or a salt thereof, and the surface modifier, the combined amount of which may at least comprise about 50%, or at least about 80%, or at least about 90%, or at least about 95%, or at least about 99% of the micro- or nano particles.

In a further aspect, the present invention is concerned with a pharmaceutical composition for administration by intramuscular or subcutaneous injection, comprising a therapeutically effective amount of TMC278, or a stereoisomer or a stereoisomeric mixture thereof, in the form of a suspension of particles consisting essentially of:
(1) TMC278, or a stereoisomer or a stereoisomeric mixture thereof in micro- or nanoparticle form, having a surface modifier adsorbed to the surface thereof; and
(2) a pharmaceutically acceptable aqueous carrier; wherein the active ingredient is suspended.

Suitable surface modifiers can be selected from known organic and inorganic pharmaceutical excipients, including various polymers, low molecular weight oligomers, natural products and surfactants. Particular surface modifiers include nonionic and anionic surfactants. Representative examples of surface modifiers include gelatin, casein, lecithin, salts of negatively charged phospholipids or the acid form thereof (such as phosphatidyl glycerol, phosphatidyl inositol, phosphatidyl serine, phosphatic acid, and their salts such as alkali metal salts, e.g. their sodium salts, for example egg phosphatidyl glycerol sodium, such as the product available under the tradename LIPOID™ EPG (egg phosphatidyl glycerol sodium), gum acacia, stearic acid, benzalkonium chloride, polyoxyethylene alkyl ethers, e.g., macrogol ethers such as cetomacrogol 1000, polyoxyethylene castor oil derivatives; polyoxyethylene stearates, colloidal silicon dioxide, sodium dodecylsulfate, carboxymethylcellulose sodium, bile salts such as sodium taurocholate, sodium desoxytaurocholate, sodium desoxycholate; methylcellulose, hydroxyethylcellulose, hydroxypropylcellulose, hydroxypropylmethylcellulose, magnesium aluminate silicate, polyvinyl alcohol (PVA), poloxamers such as PLURONIC™ F68, F108 and F127 which are block copolymers of ethylene oxide and propylene oxide; tyloxapol; Vitamin E-TGPS (α-tocopheryl polyethylene glycol succinate, in particular α-tocopheryl polyethylene glycol 1000 succinate); poloxamines, such as TETRONIC™ 908 (T908) which is a tetrafunctional block copolymer derived from sequential addition of ethylene oxide and propylene oxide to ethylenediamine; dextran; lecithin; dioctyl ester of sodium sulfosuccinic acid such as the products sold under the tradename AEROSOL OT™ (AOT) (docusate sodium); sodium lauryl sulfate (DUPONOL™ P); alkyl aryl polyether sulfonate available under the tradename TRITON™ X-200 (polyether sulfonate); polyoxyethylene sorbitan fatty acid esters (TWEENS™ 20, 40, 60 and 80); sorbitan esters of fatty acids (SPAN™ 20, 40, 60 and 80 or ARLACEL™ 20, 40, 60 and 80); polyethylene glycols (such as those sold under the tradename CARBOWAX™ 3550 and 934);

sucrose stearate and sucrose distearate mixtures such as the product available under the tradename CRODESTA™ (Sucrose Stearate (and) Sucrose Distearate) F110 or CRODESTA™ SL-40 (Sucrose Cocoate); hexyldecyl trimethyl ammonium chloride (CTAC); polyvinylpyrrolidone (PVP). If desired, two or more surface modifiers can be used in combination.

Particular surface modifiers are selected from poloxamers, α-tocopheryl polyethylene glycol succinates, polyoxyethylene sorbitan fatty acid esters, and salts of negatively charged phospholipids or the acid form thereof. More in particular the surface modifiers are selected from PLURONIC™ F108, Vitamin E TGPS, TWEEN™ 80, and LIPOID™ EPG (Egg Phosphatidyl glycerol sodium). One or more of these surface modifiers may be used. PLURONIC™ F108 corresponds to poloxamer 338 and is the polyoxyethylene, polyoxypropylene block copolymer that conforms generally to the formula HO—$[CH_2CH_2O]_x$—$[CH(CH_3)CH_2O]_y$—$[CH_2CH_2O]_z$—H in which the average values of x, y and z are respectively 128, 54 and 128. Other commercial names of poloxamer 338 are HODAG NONIONIC™ 1108-F and SYNPERONIC™ PE/F108. In one embodiment, the surface modifier comprises a combination of a polyoxyethylene sorbitan fatty acid ester and a phosphatidyl glycerol salt (in particular egg phosphatidyl glycerol sodium).

The optimal relative amount of TMC278 in relation to the surface modifier depends on the surface modifier selected, the specific surface area of the TMC278 suspension which is determined by the average effective particle size and the TMC278 concentration, the critical micelle concentration of the surface modifier if it forms micelles, etc. The relative amount (w/w) of TMC278 to the surface modifier preferably is in the range of 1:2 to about 20:1, in particular in the range of 1:1 to about 10:1, e.g. about 4:1.

The particles of this invention can be prepared by means of micronization/particle size reduction/nanonization by mechanical means and by controlled precipitation from a supersaturated solution, or by using supercritical fluids such as in the GAS technique ("gas anti-solvent"), or any combination of such techniques. In one embodiment a method is used comprising the steps of dispersing TMC278 in a liquid dispersion medium and applying mechanical means in the presence of grinding media to reduce the particle size of TMC278 to an average effective particle size of less than about 50 µm, in particular less than about 1,000 nm. The particles can be reduced in size in the presence of a surface modifier.

A general procedure for preparing the particles of this invention comprises
(a) obtaining TMC278 in micronized form;
(b) adding the micronized TMC278 to a liquid medium to form a premix/predispersion; and
(c) subjecting the premix to mechanical means in the presence of a grinding medium to reduce the average effective particle size.

TMC278 in micronized form is prepared using techniques known in the art. It is preferred that the average effective particle size of the TMC278 active agent in the predispersion be less than about 100 µm as determined by sieve analysis. Where the average effective particle size of the micronized TMC278 is greater than about 100 µm, it is preferred that the particles of the TMC278 compound be reduced in size to less than 100 µm.

The micronized TMC278 can then be added to a liquid medium in which it is essentially insoluble to form a predispersion. The concentration of TMC278 in the liquid medium (weight by weight percentage) can vary widely and depends on the selected surface modifier and other factors. Suitable concentrations of TMC278 in compositions vary between about 0.1% to about 60%, or between about 1% to about 60%, or between about 10% to about 50%, or between about 10% to about 30%, e.g. about 10%, 20% or 30% (each % in this paragraph relating to w/v).

The premix can be used directly by subjecting it to mechanical means to reduce the effective average effective particle size in the dispersion to less than 2,000 nm. It is preferred that the premix be used directly when a ball mill is used for attrition. Alternatively, TMC278 and, optionally, the surface modifier, can be dispersed in the liquid medium using suitable agitation such as, for example, a roller mill, until a homogeneous dispersion is achieved.

The mechanical means applied to reduce the effective average effective particle size of TMC278 conveniently can take the form of a dispersion mill. Suitable dispersion mills include a ball mill, an attritor/attrition mill, a vibratory mill, a planetary mill, media mills, such as a sand mill and a bead mill. A media mill is preferred due to the relatively shorter milling time required to provide the desired reduction in particle size. The beads preferably are $ZrO_2$ beads.

The grinding media for the particle size reduction step can be selected from rigid media preferably spherical or particulate in form having an average size less than 3 mm and, more preferably, less than 1 mm (as low as 200 µm beads). Such media desirably can provide the particles of the invention with shorter processing times and impart less wear to the milling equipment. Examples of grinding media are $ZrO_2$ such as 95% $ZrO_2$ stabilized with magnesia or stabilized with yttrium, zirconium silicate, glass grinding media, polymeric beads, stainless steel, titanic, alumina and the like. Preferred grinding media have a density greater than 2.5 g/cm$^3$ and include 95% $ZrO_2$ stabilized with magnesia and polymeric beads.

The attrition time can vary widely and depends primarily upon the particular mechanical means and processing conditions selected. For rolling mills, processing times of up to two days or longer may be required.

The particles should be reduced in size at a temperature that does not significantly degrade the TMC278 compound. Processing temperatures of less than 30 to 40° C. are ordinarily preferred. If desired, the processing equipment may be cooled with conventional cooling equipment. The method is conveniently carried out under conditions of ambient temperature and at processing pressures, which are safe and effective for the milling process.

The pharmaceutical compositions according to the present invention contain an aqueous carrier that preferably is pharmaceutically acceptable. Said aqueous carrier comprises sterile water optionally in admixture with other pharmaceutically acceptable ingredients. The latter comprise any ingredients for use in injectable formulations. These ingredients may be selected from one or more of a suspending agent, a buffer, a pH adjusting agent, a preservative, an isotonizing agent, and the like ingredients. In one embodiment, said ingredients are selected from one or more of a suspending agent, a buffer, a pH adjusting agent, and optionally, a preservative and an isotonizing agent. Particular ingredients may function as two or more of these agents simultaneously, e.g. behave like a preservative and a buffer, or behave like a buffer and an isotonizing agent.

Suitable buffering agents and pH adjusting agents should be used in amount sufficient to render the dispersion neutral to very slightly basic (up to pH 8.5), preferably in the pH range of 7 to 7.5. Particular buffers are the salts of week acids. Buffering and pH adjusting agents that can be added may be selected from tartaric acid, maleic acid, glycine, sodium lactate/lactic acid, ascorbic acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl) aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, including mixtures thereof.

Preservatives comprise antimicrobials and anti-oxidants which can be selected from the group consisting of benzoic acid, benzyl alcohol, butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-picolinium chloride, phenylmercuric acetate and thimerosal. Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfite, isoascorbic acid, hydroxypropyl cyclodextrin. Chelating agents include sodium citrate, sodium EDTA and malic acid.

An isotonizing agent or isotonifier may be present to ensure isotonicity of the pharmaceutical compositions of the present invention, and includes sugars such as glucose, dextrose, sucrose, fructose, trehalose, lactose; polyhydric sugar alcohols, preferably trihydric or higher sugar alcohols, such as glycerin, erythritol, arabitol, xylitol, sorbitol and mannitol. Alternatively, sodium chloride, sodium sulfate, or other appropriate inorganic salts may be used to render the solutions isotonic. These isotonifiers can be used alone or in combination. The suspensions conveniently comprise from 0 to 10% (w/v), in particular 0 to 6% of isotonizing agent. Of interest are nonionic isotonifiers, e.g. glucose, as electrolytes may affect colloidal stability.

A desirable feature for a pharmaceutical composition of the invention relates to the ease of administration. The viscosity of the pharmaceutical compositions of the invention should be sufficiently low to allow administration by injection. In particular they should be designed so that they can be taken up easily in a syringe (e.g. from a vial), injected through a fine needle (e.g. a 20 G 1½, 21 G 1½, 22 G 2 or 22 G 1¼ needle) in not too long a time span. In one embodiment the viscosity of the compositions of the invention is below about 75 mPa·s, or below 60 mPa·s. Aqueous suspensions of such viscosity or lower usually meet the above-mentioned criteria.

Ideally, the aqueous suspensions according to the present invention will comprise as much TMC278 as can be tolerated so as to keep the injected volume to a minimum, in particular from 3 to 40% (w/v), or from 3 to 30% (w/v), or from 3 to 20% (w/v), or from 10 to 30% (w/v), of TMC278. In one embodiment the aqueous suspensions of the invention contain about 10% (w/v) of TMC278, or about 10% (w/v) of TMC278, or about 30% (w/v) of TMC278.

In one embodiment, the aqueous suspensions may comprise by weight, based on the total volume of the composition:
(a) from 3% to 50% (w/v), or from 10% to 40% (w/v), or from 10% to 30% (w/v), of TMC278;
(b) from 0.5% to 10%, or from 0.5% to 2% (w/v) of a wetting agent;
(c) from 0% to 10%, or from 0% to 5%, or from 0% to 2%, or from 0% to 1% of one or more buffering agents;
(d) from 0% to 10%, or from 0% to 6% (w/v) of a isotonizing agent
(e) from 0% to 2% (w/v) preservatives; and
(f) water for injection q.s. ad 100%.

To the suspensions may optionally be added an amount of acid or base to bring the pH to a value of about pH 7. Suitable acids or bases are any of those that are physiologically acceptable, e.g. HCl, HBr, sulfuric acid, alkali metal hydroxides such as NaOH.

The administration of TMC278 as in the present invention may suffice to treat HIV infection although in a number of cases it may be recommendable to co-administer other HIV inhibitors. The latter preferably include HIV inhibitors of other classes, in particular those selected from NRTIs, PIs and fusion inhibitors. In one embodiment, the other HIV inhibitor that is co-administered is a PI inhibitor. HIV inhibitors that may be co-administered by preference are those used in HAART combinations comprising an NNRTI. For example two further NRTIs or an NRTI and a PI may be co-administered. Such co-administration may be by oral administration or parenterally.

In certain instances, the treatment of HIV infection may be limited to only the administration of a composition of TMC278 in accordance with this invention, i.e. as monotherapy without co-administration of further HIV inhibitors. This option may be recommended, for example, where the viral load is relatively low, for example where the viral load (represented as the number of copies of viral RNA in a specified volume of serum) is below about 200 copies/ml, in particular below about 100 copies/ml, more in particular below 50 copies/ml, specifically below the detection limit of the virus. In one embodiment, this type of monotherapy is applied after initial treatment with a combination of HIV drugs, in particular with any of the HAART combinations during a certain period of time until the viral load in blood plasma reaches the afore mentioned low viral level.

In a further aspect the present invention relates to the use of a pharmaceutical composition comprising an anti-virally effective amount of TMC278 or a pharmaceutically acceptable acid-addition salt thereof, in accordance with the present invention, for the manufacture of a medicament for maintenance therapy of a subject being infected with HIV, wherein the composition is administered or is to be administered intermittently at a time interval that is in the range of one week to one year, or one week to two years.

Thus in a further aspect, the present invention provides a method for the long term treatment of a patient being infected with HIV, said method comprising
(i) the treatment of said patient with a combination of HIV inhibitors; followed by
(ii) the intermittent administration of a pharmaceutical composition comprising an anti-virally effective amount of TMC278 or a pharmaceutically acceptable acid-addition salt thereof, in accordance with the present invention, wherein the composition is administered at a time interval of at least one week.

The present invention also concerns a pharmaceutical composition as described hereinbefore for use as a medicament in the treatment or prophylaxis of HIV infection.

In addition, the present invention concerns the use of a pharmaceutical composition as described herein for the preparation of a medicament for the prophylaxis or treatment of HIV infection.

The present invention further concerns a method of treating a subject infected with HIV, said method comprising the administration of a therapeutically effective amount of a pharmaceutical composition as described herein.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

The following examples are intended to illustrate the present invention and should not be construed as limiting the invention thereto.

Example 1

Preparation of Nanosuspensions

Glass bottles of 250 ml and $ZrO_2$ beads, used as the milling media, were sterilized in an autoclave. Five grams of drug substance were put into the 250 ml glass bottle as well as a solution of 1.25 g PLURONIC™ F108 in 60 ml of water for injection. Three hundred grams of $ZrO_2$-beads with an average particle size of 500 μm were added. The bottle was placed on a roller mill. The suspension was micronized at 100 rpm during 72 hours. At the end of the milling process the concentrated nanosuspension was removed with a syringe and filled into vials. The resulting formulation is Formulation 1 in the following table. Determination of the concentration was done by HPLC/UV. A dilution was made to a final concentration of 25 mg/ml of TMC278. The resulting suspension was shielded from light.

Using similar procedures, Formulations 2, 3 and 4 were prepared. These were titrated with sodium hydroxide 1N solution to a pH of about 7. In formulations 2, 3 and 4 the LIPOID™ EPG (Egg Phosphatidyl glycerol sodium) is solubilized in the TWEEN™ 80.

| Ingredient | Formula 1 | Formula 2 | Formula 3 | Formula 4 |
|---|---|---|---|---|
| TMC278 | 5 g | 300 mg | 300 mg | 300 mg |
| PLURONIC™ F108 | 1.25 g | — | — | — |
| TWEEN™ 80 | — | 75 mg | 75 mg | 75 mg |
| LIPOID™ EPG (Egg Phosphatidyl glycerol sodium) | — | 9.375 mg | 9.375 mg | 9.375 mg |
| Glucose | — | 50 mg | 50 mg | 50 mg |
| $NaH_2PO_4$·1aq | — | — | 2 mg | 2 mg |
| citric acid·1aq | — | — | — | 1 mg |
| NaOH 1N | — | at pH 6.72 | at pH 6.98 | at pH 6.99 |

Example 2

Kinetic Study

The present study demonstrates that an injectable formulation of nanonised TMC278 or its HCl-salt results in stable blood plasma levels during a prolonged period of time. This study compares the plasma kinetics of TMC278 base and hydrochloric salt after single intramuscular (IM) or subcutaneous injection of a nanosuspension (Formula 1 of the previous example) at 5 mg/kg in male beagle dogs.

Six healthy male beagle dogs with body weights ranging from 8 to 16 kg at the start of the study, were used. Each dog was identified by an ear tattoo number. Two dogs were dosed intramuscularly (IM) in the left and right m. biceps femoris (treatment group A). Two dogs were dosed IM with TMC278.HCl (treatment group B). Two dogs were dosed subcutaneously (SC) in the left and right thoracal region. The injection volume was 2×0.1 ml/kg in all treatment groups. A 20 G needle was used.

Blood samples of 3 ml were taken from the left jugular vein from all dogs on day 0 at 0 h (predose), 20 min, 1 h, 3 h, 8 h and 24 h post-dose and further on days 2, 3, 6, 8, 10, 13, 16, 20, 23, 27, 29, 36, 43, 50, 57, 64, 71, 78, 85 and 92 at approximately 8 AM. Blood samples were placed on EDTA, EDTA Vacuette Greiner, Cat. No. 454086, Greiner Labortechnik N.V.). Within 2 h of blood sampling, samples were centrifuged at room temperature at about 1900×g for 10 minutes to allow plasma separation. Plasma was immediately transferred into a second tube and stored in the freezer within 2 hours after the start of centrifugation. Plasma samples were analysed individually for TMC278 by means of a validated LC-MS/MS-method.

TABLE 1

Individual and mean plasma concentrations and some basic pharmacokineticparameters of TMC278 in male beagle dogs after single IM administration of a nanosuspension of TMC278 at 5 mg/kg

| Treatment group | | A | | |
|---|---|---|---|---|
| Compound | | TMC278 | | |
| Dose (mg/kg) | | 5 | | |
| Adm. Route | | IM | | |
| Time (h) | DogNo | 17264 | 18186 | Mean |
| 0 (d0) | | <1.00 | <1.00 | <1.00 |
| 0.33 | | 121 | 186 | 154 |
| 1 | | 110 | 82.6 | 96.3 |
| 3 | | 131 | 145 | 138 |
| 8 | | 130 | 136 | 133 |
| 24 (d1) | | 150 | 120 | 135 |
| 48 (d2) | | 159 | 132 | 146 |
| 72 (d3) | | 115 | 99.6 | 107 |
| 144 (d6) | | 86.2 | 91.9 | 89.1 |
| 192 (d8) | | 72.4 | 75.5 | 74.0 |
| 240 (d10) | | 56.7 | 62.5 | 59.6 |
| 312 (d13) | | 33.4 | 38.0 | 35.7 |
| 384 (d16) | | 23.9 | 20.6 | 22.3 |
| 480 (d20) | | 20.5 | 16.6 | 18.6 |
| 648 (d27) | | 11.4 | 9.08 | 10.2 |
| 696 (d29) | | 11.3 | 11.2 | 11.3 |
| 864 (d36) | | 7.33 | 6.44 | 6.89 |
| 1032 (d43) | | 5.19 | 5.18 | 5.19 |
| 1200 (d50) | | 3.40 | 3.25 | 3.33 |
| 1368 (d57) | | 3.00 | 3.00 | 3.00 |
| 1536 (d64) | | 2.84 | 2.44 | 2.64 |
| 1704 (d71) | | 2.48 | 1.84 | 2.16 |
| 1872 (d78) | | 1.79 | 1.45 | 1.62 |
| 2040 (d85) | | 1.99 | 1.61 | 1.80 |
| 2208 (d92) | | 1.56 | 1.25 | 1.41 |
| Cmax (ng/ml) | | 159 | 186 | 173 |
| Tmax (h) | | 48 | 0.33 | 24 |
| AUC0-312 h (ng · h/ml) | | 27400 | 26600 | 27000 |
| AUC0-696 h (ng · h/ml) | | 34800 | 33000 | 33900 |
| AUC0-2208 h (ng · h/ml) | | 40500 | 38200 | 39400 |

TABLE 2

Individual and mean plasma concentrations and some basic pharmacokinetic parameters of TMC278 in male beagle dogs after single IM administration of a nanosuspension of TMC278•HCl at 5 mg (eq.)/kg

| Treatment group | | B | | |
|---|---|---|---|---|
| Compound | | TMC278.HCl | | |
| Dose (mg eq./kg) | | 5 | | |
| Adm. Route | | IM | | |
| Time (h) | DogNo | 19072 | 19080 | Mean |
| 0 | (d0) | <1.00 | <1.00 | <1.00 |
| 0.33 | | 4.42 | 4.68 | 4.55 |
| 1 | | 7.80 | 7.19 | 7.50 |
| 3 | | 14.7 | 16.3 | 15.5 |
| 8 | | 32.2 | 27.1 | 29.7 |
| 24 | (d1) | 50.1 | 69.8 | 60.0 |
| 48 | (d2) | 85.6 | 105 | 95.3 |
| 72 | (d3) | 47.5 | 69.5 | 58.5 |
| 144 | (d6) | 48.3 | 62.3 | 55.3 |
| 192 | (d8) | 46.8 | 65.8 | 56.3 |
| 240 | (d10) | 55.7 | 82.2 | 69.0 |
| 312 | (d13) | 27.0 | 45.8 | 36.4 |
| 384 | (d16) | 17.0 | 31.9 | 24.5 |
| 480 | (d20) | 13.7 | 25.5 | 19.6 |
| 648 | (d27) | 7.91 | 14.4 | 11.2 |
| 696 | (d29) | 10.2 | 18.8 | 14.5 |
| 864 | (d36) | 6.18 | 11.4 | 8.79 |
| 1032 | (d43) | 6.32 | 8.18 | 7.25 |
| 1200 | (d50) | 4.56 | 5.68 | 5.12 |
| 1368 | (d57) | 4.73 | 5.08 | 4.91 |
| 1536 | (d64) | 4.47 | 4.43 | 4.45 |
| 1704 | (d71) | 3.38 | 3.90 | 3.64 |
| 1872 | (d78) | 3.12 | 3.20 | 3.16 |
| 2040 | (d85) | 3.20 | 4.00 | 3.60 |
| 2208 | (d92) | 2.96 | 2.81 | 2.89 |
| Cmax (ng/ml) | | 85.6 | 105 | 95.3 |
| Tmax (h) | | 48 | 48 | 48 |
| AUC0-312 h (ng · h/ml) | | 15000 | 20900 | 18000 |
| AUC0-696 h (ng · h/ml) | | 20300 | 30500 | 25400 |
| AUC0-2208 h (ng · h/ml) | | 27400 | 39900 | 33600 |

TABLE 3

Individual and mean plasma concentrations and some basic pharmacokinetic parameters of TMC278 in male beagle dogs after single SC administration of a nanosuspension of TMC278 at 5 mg/kg

| Treatment group | | C | | |
|---|---|---|---|---|
| Compound | | TMC278 | | |
| Dose (mg/kg) | | 5 | | |
| Adm. Route | | SC | | |
| Time (h) | DogNo | 19129 | 19349 | Mean |
| 0 | (d0) | <1.00 | <1.00 | <1.00 |
| 0.33 | | <1.00 | <1.00 | <1.00 |
| 1 | | 1.62 | 1.37 | 1.50 |
| 3 | | 7.96 | 8.42 | 8.19 |
| 8 | | 27.6 | 13.8 | 20.7 |
| 24 | (d1) | 15.7 | 28.5 | 22.1 |
| 48 | (d2) | 34.8 | 29.1 | 32.0 |
| 72 | (d3) | 26.1 | 30.6 | 28.4 |
| 144 | (d6) | 18.9 | 32.7 | 25.8 |
| 192 | (d8) | 17.7 | 23.0 | 20.4 |
| 240 | (d10) | 24.3 | 42.0 | 33.2 |
| 312 | (d13) | 21.7 | 38.8 | 30.3 |
| 384 | (d16) | 21.7 | 16.6 | 19.2 |
| 480 | (d20) | 29.8 | 21.2 | 25.5 |
| 648 | (d27) | 19.0 | 11.0 | 15.0 |
| 696 | (d29) | 21.0 | 10.5 | 15.8 |
| 864 | (d36) | 12.7 | 5.49 | 9.10 |
| 1032 | (d43) | 5.22 | 6.03 | 5.63 |
| 1200 | (d50) | 6.37 | 3.40 | 4.89 |
| 1368 | (d57) | 4.78 | 2.52 | 3.65 |
| 1536 | (d64) | 6.45 | 2.05 | 4.25 |
| 1704 | (d71) | 3.96 | 3.57 | 3.77 |
| 1872 | (d78) | 3.66 | 1.91 | 2.79 |
| 2040 | (d85) | 8.60 | 2.82 | 5.71 |
| 2208 | (d92) | 3.05 | 2.49 | 2.77 |
| Cmax (ng/ml) | | 34.8 | 42.0 | 38.4 |
| Tmax (h) | | 48 | 240 | 144 |
| AUC0-312 h (ng · h/ml) | | 6910 | 9880 | 8400 |
| AUC0-696 h (ng · h/ml) | | 15900 | 16700 | 16300 |
| AUC0-2208 h (ng · h/ml) | | 26400 | 22400 | 24400 |

The invention claimed is:

1. A method for producing blood plasma levels of 4-[[4-[[4-(2-cyanoethenyl)-2,6-dimethylphenyl]amino]-2-pyrimidinyl]amino]benzonitrile (TMC278) that are sufficient to treat an HIV infection in an HIV-infected patient comprising:
   administering to the patient, by intramuscular or subcutaneous injection, an aqueous suspension comprising nanoparticles of 4-[[4-[[4-(2-cyanoethenyl)-2,6-dimethylphenyl]amino]-2-pyrimidinyl]amino]benzonitrile (TMC278), or a salt, a stereoisomer or a stereoisomeric mixture thereof,
       the particles having a poloxamer adsorbed onto the surfaces thereof, and
       the particles having an average effective particle size of below about 1000 nm;
   wherein the aqueous suspension is administered intermittently at a time interval that is once every four weeks or once every month; and
   wherein the amount of TMC278, or the salt, stereoisomer, or stereoisomeric mixture thereof, in the aqueous suspension is effective in producing a blood plasma level of TMC278 that is sufficient to treat the HIV infection in the patient during the time interval.

2. The method of claim 1, wherein the amount is calculated on a basis of about 5 mg/day to about 50 mg/day of TMC278.

3. The method of claim 2, wherein the amount is calculated on a basis of about 10 mg/day to about 25 mg/day.

4. The method of claim 1, wherein TMC278 is present in base form or in an acid addition salt form.

5. The method of claim 1, wherein the poloxamer is poloxamer 338.

6. The method of claim 5, wherein the average effective particle size of the nanoparticles is about 50 nm to about 1000 nm.

7. The method of claim 1, wherein the amount of TMC278 corresponds with a monthly dose of
   a. from about 150 mg to about 1500 mg;
   b. from about 30 mg to about 300 mg; or
   c. about 300 mg.

8. The method of claim 1, wherein the aqueous suspension comprises by weight based on the total volume of the composition:
   a. from 3% to 50%, from 10% to 40% or from 10 to 30%, of TMC278
   b. from 0.5% to 10% or from 0.5% to 2% of the poloxamer;

c. from 0% to 10%, from 0% to 5%, from 0% to 2%, or from 0% to 1% of one of more buffering agents;

d. from 0% to 10%, or from 0% to 6% of an isotonizing agent;

e. from 0% to 2% preservatives; and f. water for injection q.s. ad 100%.

9. The method of claim 4, wherein TMC278 is present as the E-isomer of the base form.

10. The method of claim 4, wherein TMC278 is present as the E-isomer of the acid addition salt form.

11. The method of claim 8, wherein the buffering agent is tartaric acid, maleic acid, glycine, sodium lactate, lactic acid, ascorbic acid, sodium citrates, citric acid, sodium acetate, acetic acid, sodium bicarbonate, carbonic acid, sodium succinate, succinic acid, sodium benzoate, benzoic acid, sodium phosphates, tris(hydroxymethyl)aminomethane, sodium bicarbonate, sodium carbonate, ammonium hydroxide, benzene sulfonic acid, benzoate sodium, benzoate acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, or a mixture of at least two buffering agents.

12. The method of claim 8, wherein the isotonizing agent is glucose, dextrose, sucrose, fructose, trehalose, lactose, a polyhydric sugar alcohol, a trihydric or higher sugar alcohol, glycerin, erythritol, arabitol, xylitol, sorbitol, mannitol, sodium chloride or sodium sulfate.

13. The method of claim 1, wherein the amount of TMC278 is calculated on a basis of about 10 mg/day to about 25 mg/day, TMC278 is present as the E-isomer of the base form, and wherein the poloxamer is poloxamer 338.

14. The method of claim 1, wherein the average effective nanoparticle size is from about 150 nm to about 220 nm.

15. The method of claim 1, wherein the relative amount by weight (w/w) of TMC278 to the poloxamer is in the range of 1:2 to about 20:1.

16. The method of claim 15, wherein the relative amount by weight (w/w) of TMC278 to the poloxamer is about 1:1, about 1:2, about 4:1, about 10:1 or about 20:1.

17. The method of claim 16, wherein the aqueous suspension is administered by intramuscular injection.

18. The method of claim 17, wherein the aqueous suspension is administered by intramuscular injection once every four weeks.

19. The method of claim 17, wherein the aqueous suspension is administered by intramuscular injection once every month.

20. The method of claim 1, wherein the average effective nanoparticle size is from about 50 nm to about 400 nm.

21. The method of claim 1, wherein the average effective nanoparticle size is from about 50 nm to about 250 nm.

22. The method of claim 1, wherein the average effective nanoparticle size is about 400 nm.

23. The method of claim 1, wherein the average effective nanoparticle size is about 200 nm.

* * * * *

UNITED STATES PATENT AND TRADEMARK OFFICE
CERTIFICATE OF CORRECTION

PATENT NO. : 11,389,447 B2  
APPLICATION NO. : 14/964297  
DATED : July 19, 2022  
INVENTOR(S) : Lieven Elvire Colette Baert et al.

It is certified that error appears in the above-identified patent and that said Letters Patent is hereby corrected as shown below:

On the Title Page

Item (30), currently reads:  
"Foreign Application Priority Data  
Jun. 23, 2006 (EP).............06115398"

Should read the following:  
--Foreign Application Priority Data  
Jun. 23, 2006 (EP).............06115938--

Signed and Sealed this  
Twenty-eighth Day of May, 2024

Katherine Kelly Vidal  
*Director of the United States Patent and Trademark Office*